United States Patent [19]

Adler et al.

[11] Patent Number: 5,106,758
[45] Date of Patent: Apr. 21, 1992

[54] ANALYTICAL TEST DEVICE AND THE USE THEREOF

[75] Inventors: Stanford L. Adler, Warwick, N.Y.; John Campisi, Riverside, Conn.; Koon-Wah Leong, Ossining, N.Y.

[73] Assignee: Technicon Instruments Corporation, Tarrytown, N.Y.

[21] Appl. No.: 282,657

[22] Filed: Dec. 12, 1988

[51] Int. Cl.$^5$ ............................................. G01N 21/00
[52] U.S. Cl. ................................. 436/165; 436/178; 422/56; 422/57; 422/58; 435/7.1
[58] Field of Search ............................. 436/165, 178; 422/56-58; 435/7.1

[56] References Cited

U.S. PATENT DOCUMENTS

| | | | |
|---|---|---|---|
| 4,323,536 | 4/1982 | Columbus | 422/56 |
| 4,668,472 | 5/1987 | Sakamoto et al. | 422/56 |
| 4,717,656 | 1/1988 | Swanljung | 435/7 |
| 4,738,823 | 4/1988 | Engelmann | 422/56 |
| 4,920,046 | 4/1990 | McFarland et al. | 422/56 |

Primary Examiner—Robert J. Warden
Assistant Examiner—Laura E. Collins
Attorney, Agent, or Firm—Jeffrey M. Greenman

[57] ABSTRACT

The analytical device includes a base adapted to support a porous member having dispersed throughout at least one analyte responsive substance which undergoes a detectable response to the presence and concentration of the analyte in the test sample. A cover integral with the base is provided with a reaction well adapted for storing a dried reaction component and for receiving the liquid test sample deposited on the analytical device whereby the liquid test sample and the reaction component form a liquid reaction mixture therein. A passage is included in the reaction well for selectively transferring the reaction mixture therethrough. This passage is normally spaced from the porous member and effectively closed to transfer therethrough of the reaction mixture, and is selectively movable toward the porous member to effectively open to passage therethrough of the reaction mixture whereby the analyte responsive substance will undergo a detectable response to the analyte present in the liquid reaction mixture. The base is provided with a suitable viewing port to permit monitoring of the detectable response generated as a result of the at least one analyte responsive substance interacting with the analyte in the test sample. Such a detectable response may be detected by appropriate photometric or colorimetric apparatus.

9 Claims, 6 Drawing Sheets

DCT THEOPHYLLINE ASSAY CORRELATION STUDY

ANALYTICAL TEST DEVICE AND THE USE THEREOF

BACKGROUND OF THE INVENTION

1. Field of the Invention

This invention relates to the art of sample liquid analysis and, more particularly, to a new and improved analytical device for performing dry chemistry analysis of aqueous fluids. As used herein, dry chemistry analysis refers to analytical methods and techniques that are carried out using chemical reagents contained in various "dry-to-the-touch" test elements such as single layer or multilayer test elements and the like.

2. Description of the Prior Art

An increasingly large number of analytical tests, procedures and analysis, i.e., assays, must be performed each day on many kinds of liquid samples, including, but not limited to aqueous biological fluids such as blood, serum, urine, cerebrospinal fluid and the like. Various methods have been developed for conducting such analysis, including those known in the art as dry chemistry analysis techniques.

A prolific dry chemistry analytical element and one form most readily adaptable for use in automated sample liquid analysis systems is the multilayer test element. Traditional multilayer analysis techniques rely on film technology wherein reagents are applied to a transparent film supported in layers. Such multilayer devices, which are well known in the art, may consist of one or more spreading layers, reaction layers, separation layers and detection layers superimposed one on the other, according to the analyte to be detected and the method of analysis used. These multilayer analytical elements are typically custom designed to the particular assay to be performed. That is, there is generally no generic structure that can be adopted for such an analytical element, and the number of different analytes that can be detected using a multilayer element of a particular construction is limited.

Generally speaking, to perform an assay using a typical multilayer test element, a sample of body fluid is applied to a spreading layer to assure even distribution of the sample to an underlying reaction layer which may contain a reagent component. This liquid sample and first reagent mixture then passes into a second underlying layer for reaction with additional reagent components. Since the reagent containing layers may be in contact with each other the cross migration of their respective reagent components and hence the potential of unintentional contamination of each layer exists. Generally, devices so constructed do not allow for the performance of sequential operation. The liquid sample and liquid sample reagent mixture will flow from one layer to the contiguous layer unless a separate timing layer is provided therebetween. The timing layer retains for a certain period of time the liquid in the top layer until the reaction is substantially completed and then releases the resulting reaction product to diffuse into the underlying layer.

The desirability of maintaining the reagent containing layers in spaced relationship to each other to minimize contamination and to provide some control over the timing of the assay sequence has been recognized in the art. Multilayer analytical devices have been provided wherein a liquid test sample contacts a reagent in a first reagent layer, with this layer adapted to thereafter be brought into contact with a second layer by moving the first and second layers into fluid contact with each other when a certain stage in the reaction is reached. See, for example, U.S. Pat. Nos. 4,258,001 and 4,357,363, both assigned to Eastman Kodak Company in which multilayer dry chemistry analytical elements are disclosed. In one embodiment the analytical element contains two layers or zones carried on a support. The zones are initially spaced apart by a spacer means. Under conditions of use, these zones are brought into contact such as by application of suitable compressive force to the upper zone which causes the pressure-deformable spacer means to deform resulting in the upper zone being moved into fluid contact with the lower zone. There is no indication in either reference, however, as to whether the zones are brought into fluid contact after the reaction sequence is completed, although the language in the respective disclosures suggests fluid contact between the zones occurs substantially at the time of sample application.

The need to control the sequential interaction of the test sample with various reagents, while being important in some chemical assays, is of necessity when considering immuno-chemical analysis wherein the antibodies, enzymes and substrates in the reagents must be segregated during storage, introduced into the sample or the reaction mixture at the proper time and in the proper sequence.

While various proposals have been made with respect to multilayer analysis element utilizing chemical reactions, only a few recent proposals have been made with respect to such multilayer analysis films in which reagents or immunological reaction are incorporated. See, for example, U.S. Pat. No. 4,58,12 assigned to Fuji Photo Film, Co., and the references cited therein. When one attempts to apply immunological reaction techniques to conventional multilayer analysis films, it is difficult to obtain satisfactory analysis data due to problems inherent to immunological analysis as discussed in this reference.

In the aforementioned U.S. Pat. No. 4,587,102 a dry type multilayer analysis element for assaying a concentration of a specific component utilizing a competitive immunological reaction is disclosed. The analysis element contains a detection element comprising a detection layer which receives a labelled complex formed as a result of the competitive immunological reaction, or an optically detectable change dependent upon an amount of the labelled complex of the specific component. Further provided on the detection layer is a reaction layer comprising a fibrous porous medium containing fine particles. While this device attempts to address the problems inherent with immuno-chemical analysis utilizing multilayer analytical elements, it is still a comparatively complex structure requiring many different components and is utilizable only for a limited number of different assay protocols.

There is disclosed in U.S. Pat. No. 4,717,656 assigned to Vertrik Bioteknik AB, a device for chemical analysis which consists essentially of a series of interconnected segments wherein a sample to be tested is contacted with reagents reacting with the sample to form a detectable substance which in turn is detected for a qualitative or quantitative determination. Essentially, the device is a test kit for performing an analysis wherein all chemically active parts which are necessary for carrying out the analysis are built into the device. These chemically active parts are arranged or mounted in such a way that they are connected with the sample and each other by simple folding system. While this device permits the timed, sequential performance of the assay, the physical manipulations of the various segments as required in this device make it totally unusable in an automated analysis system.

U.S. Pat. No. 4,288,228 assigned to the assignee hereof, discloses whole blood analysis and diffusion apparatus therefor. In one embodiment, a precise aliquot is obtained by a carefully controlled cross-diffusion between the porous media via a molecular diffusion switch. The molecular switch achieves accurately timed diffusion of substances from one medium to another, such that an amount (aliquot) of material may be accurately and precisely transferred. The molecular switch is comprised of an impermeable layer which acts as a barrier or isolating means between two porous media. Preferably, this impermeable layer is an immiscible fluid (i.e., gas or liquid) which is easily displaced from between the porous media, and then restored therebetween. Although providing for a timed reaction, this device would not be readily adaptable for use in an automated clinical analyzer.

OBJECTS OF THE INVENTION

It is, accordingly, an object of our invention to provide a new and improved analytical device for performing dry chemistry analysis.

It is another object of our invention to provide an analytical device as above which permits the timed selective interaction of the liquid test sample and reagent components carried in the device.

It is a further object of our invention to provide an analytical device as above which is particularly adapted for use in automated sample liquid analysis systems.

It is yet another object of our invention to provide an analytical element as above of a generic physical structure which can be utilized in a wide variety of analysis, including immuno-chemical analysis.

It is a further object of our invention to provide an analytical device as above which is simply and inexpensively fabricatible from readily available, inexpensive materials.

It is another object of our invention to provide an analytical device as above which is so highly reliable as to be virtually fail safe in operation.

Other objects and features of our invention will be in part apparent and in part pointed out hereinafter.

SUMMARY OF THE INVENTION

The new and improved analytical device for the quantitative and qualitative determination of an analyte in a liquid test sample in accordance with our invention includes a base adapted to support a reagent containing means. Preferably, this reagent containing means is a porous member having dispersed throughout at least one analyte responsive substance in a dry state which undergoes a detectable response to the presence and concentration of the analyte in the test sample.

Integral with the base is a cover or support member adapted for storing a reaction component therein. This reaction component can include a substance which physically changes the sample, such as a cytolytic agent, to release an analyte for detection, or may be a reagent component which is responsive to the analyte to form a reaction product, which when coming into contact with at least one analyte responsive substance in the porous member, generates a detectable response. The reaction component which is preferably in the dry state, is retained in a reaction well in the cover which is adapted to receive the liquid test sample deposited on the analytical device whereby the liquid test sample and the dry reaction component mix to form a liquid reaction mixture within the reaction well.

The reaction well includes a passage means therein for selectively transferring the reaction mixture therethrough. This passage means is normally spaced from the porous member and is effectively closed to transfer therethrough of the liquid reaction mixture held in the reaction well, and is selectively movable toward the porous member to effectively open to passage therethrough of the reaction mixture to the porous member whereby the analyte responsive substance will undergo a detectable response to the analyte present in the liquid reaction mixture.

The passage means may be at least one opening in the reagent well with the passage means and reagent well dimensioned such that the surface tension of the liquid reaction mixture with the walls of the opening and the reaction well prevents the liquid reaction mixture held in the reaction well from transfer through the passage means to the porous member. When the passage means is moved into engagement with the porous member, the liquid reaction mixture held within the reaction well by surface tension is drawn through the passage by capillary attraction.

In another configuration, the passage means includes a transverse or bottom wall in the reaction well which contains one or more openings that are normally substantially closed. As the passage means is moved into engagement with the porous member, the openings in the transverse wall open to permit the flow of liquid contained in the reaction well into the passage means. The openings may be arcuate or radial slits in the transverse wall.

The base is provided with a suitable viewing port to permit monitoring of the detectable response generated as a result of the at least one analyte responsive substance interacting with the analyte in the test sample. Such a detectable response may be detected by appropriate photometric or colorimetric apparatus.

By measuring the detectable response produced by the analyte responsive substance and comparing the detectable response so produced with the detectable response produced when the analysis is conducted with a series of standard compositions containing known amounts of analyte, the qualitative and quantitative determination of analyte in the test sample can be made.

DESCRIPTION OF THE DRAWINGS

The above and other objects and significant advantages of the present invention are believed made clear by the following detailed description thereof taken in conjunction with the accompanying drawings wherein.

DETAILED DESCRIPTION OF THE INVENTION

Referring now to the drawings, a new and improved analytical device configured and operable in accordance with one embodiment of the teachings of our present invention is generally identified by reference numeral 10. As will be described in detail hereinafter, the analytical device 10 is adapted for containing two substances or reagents initially in spaced relationship from one another, and thereafter bring these substances into fluid contact either sequentially or concurrently in the presence of a liquid test sample to perform an assay. The present invention is applicable to analysis for the quantitative and qualitative determination of an analyte in a test sample wherein the sample to be tested is contacted with reagent(s) responsive to the presence and concentration of analyte in the sample to form a detectable response. The detectable responses is meant to refer to a detectable change that is directly or indirectly indicative of the presence and/or concentration of the analyte.

Unless otherwise indicated, all components of the analytical devices are formed of a durable, resilient plastic material such as polyvinyl chloride (PVC), polystyrene, polyester, or cellulosic polymers and copolymers, and the like. The plastic components may be thermoformed from sheet materials, although other manufacturing methods known in the plastic forming art may be used.

Figure 1:
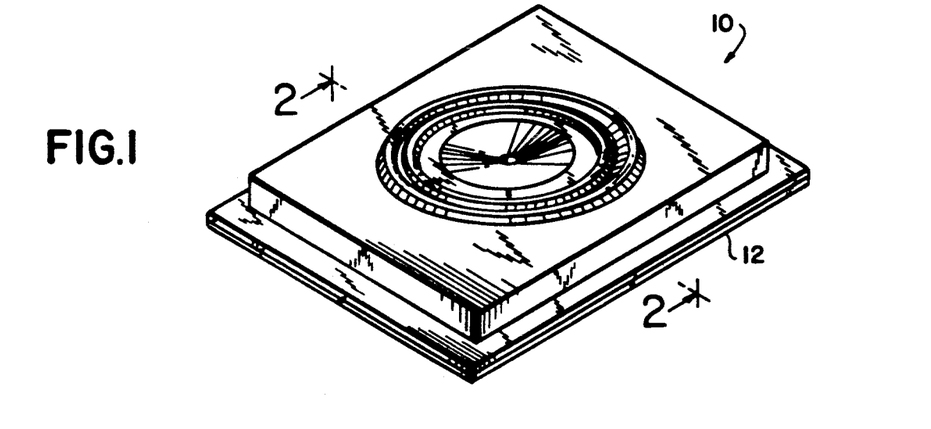
FIG. 1 is a perspective view of a new and improved analytical device configured and operable in accordance with the teachings of our invention.
Figure 2:
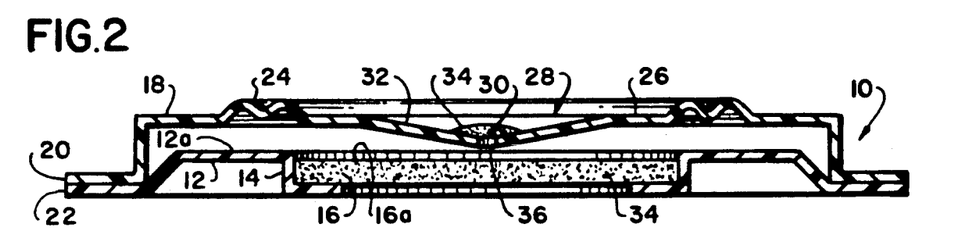
FIG. 2 is a cross-sectional view taken generally along line 2—2 in FIG. 1.

With reference to FIG. 2, the analytical device 10 includes a base 12 of any suitable peripheral shape, including circular or polygonal, which is provided with a recess 14 therein for closely receiving a porous member 16. The upper surface 16a of the porous member may rest below the upper surface 12a when the porous member is positioned within the recess to create a rim which serves to prevent the overflow into the interior of the analytical device of liquid deposited on the porous member, as will hereinafter be described. It will be apparent that the recess 14 and porous member 16 may have a peripheral shape compatible with the base 12. Obviously, small projections or dimples, not shown, can be formed in the periphery of recess 14 to retain porous member 16 therein. The base 12 should be of sufficient thickness for it to provide support for the porous member 16. Strictly by way of example, and not by way of limitation, the base 12 may have a material thickness of about 0.020 inch.

Porous member 16 can take many forms and be of many different materials including, but not necessarily limited to, paper, woven and non-woven fabrics, porous polyethylene, porous ceramics and other foamed plastics. The material for porous member 16 may be of an open cell-type and, in a preferred arrangement, is an open cell reticulated foam having an interconnecting lattice structure. Such material may have a three dimensional, interconnected cell structure that is about 95% void volume, and with approximately 50 cells per square inch. This material has ideal physical properties including a very large surface area to volume ratio, a large liquid hold-up volume, and can be made hydrophilic. The lattice structure assures uniform distribution of a solution throughout the volume of the porous member. In addition, the material is at least 90% transparent to visible light in thin sections of about one-eighth inch thick. As described in the experiments hereinbelow, a suitable porous material is a polymer material obtained from Porex Technologies of Fairburn, Ga, having an average 35 to 50 micron pore size.

The base 12 includes a cover member 18 which cooperates with the base 12. The cover member 18 is complimentary to the shape of the base 12 and may be provided with a peripheral flange 20 which can be bonded, ultrasonically welded or otherwise suitably secured to the peripheral flange 22 on the base 12. For the desired flexibility, the importance of which will become readily apparent, the cover member 18 is formed from a relatively thin material, for example, a PVC sheet of 0.010 inch thickness. For added flexibility, the cover member may be provided with a series of corrugations 24 to provide for the radial extension needed for displacement of the central portion 26 of the cover 18 towards the porous member 16.

One possible use of the analytical device 10 is in automated clinical analyzers and the base 12 and cover 18 may be contoured as to permit stacking of individual devices within a loading magazine in such an instrument, as well as to permit ready removal of each device therefrom. It will be appreciated that such analytical apparatus form no part of our present invention.

The central position of the cover 18 is provided with a reaction well and passage means generally referred to by the reference numerals 28 and 30 respectively which are constructed to selectively release liquid contained in the reaction well 28 through the passage means 30 to the porous member 16 as will be described below.

In accordance with one embodiment of our invention, the reaction well 28 is a central depression or funnel 32 in the central portion 26 of cover 18, defining storage means for a dry substance or reaction component 34. As noted above, passage means in the form of an opening 36 is provided in the reaction well 28 for selective transfer of a liquid within the reaction well into the porous member 16. In this embodiment, the opening 36 is sized such that surface tension between the liquid in the reaction well and the walls of the reaction well normally prevents movement of a liquid therethrough. For example, the opening may have a maximum diameter of 0.046 inch.

The cover 18 may be representatively constituted as described by a suitable plastic which is normally hydrophobic, and it has been determined in further accordance with the teaching of our invention that the plastic must be appropriately formulated, or treated with surfactant after formulation, to render the same hydrophilic thus providing for the uniform distribution of the liquid in the reaction well as will be described.

In addition, the surface energy of the material from which the cover is formed should be such, that when compared to the surface tension of the liquid, the resulting net force will act to retain the liquid in the reaction well and prevent it from flowing through the opening. Note, however, that this force must not override the capillary attraction force created when the liquid comes into contact with the porous member 16 as will be described to have the undesired effect of hindering flow of the liquid into the porous member.

Characteristic of the present invention is that an analyte responsive substance 38 which undergoes a detectable response to the presence and concentration of the analyte in the test sample be dispersed throughout the porous member. It will be appreciated that the analyte responsive substance may be a mixture of two or more substances which together, form a reagent component for the assay to be performed. Preferably, this analyte responsive substance 38 is dried within the voids in lattice structure of porous member 16. For example, about thirty-five (35) microliters of a solution of the analyte responsive substance may be deposited on the porous member. Due to the substantial void volume within the porous member, the liquid analyte responsive substance readily disperses therethrough by capillary action due to the interconnection lattice structure. The porous member may then be subjected to lyophilization for evaporation of the liquid therefrom resulting in a very thin film or coating of the dry analyte responsive substance being formed on the internal surfaces of the porous member The thin film or coating is such that it accompanies less than 10% of the void volume of the porous member. It should be noted that the liquid analyte responsive substance may be applied and evaporated from the porous member before or after it is placed in the recess of the base.

The second substance or reaction component 34 intended to react with the test sample before the analyte comes into contact with the analyte responsive substance may be provided on the cover 18 as follows. An aqueous solution of the substance is deposited in the reaction well 28, but will not flow through the opening 36 due to the surface tension between the liquid and walls of the reaction well discussed above. The liquid is thereafter evaporated, for example by lyophilization, resulting in a dry film or deposit being formed in the reagent well.

Figure 6:
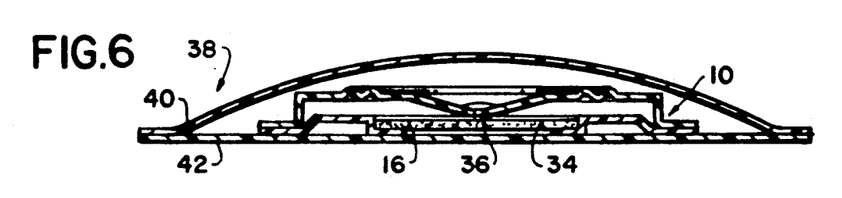
FIG. 6 is a cross-sectional elevational view of a sealed package containing the analytical device of FIGS. 1–5.

If desired, the analytical device 10 may be sealed within a package 38 as shown in FIG. 6 until the device is ready for use to maintain the integrity of the reaction component and analyte responsive reagent. The package 38 can be in the form of metal or plastic foil sheets 40, 42 peripherally sealed together.

Figure 3:
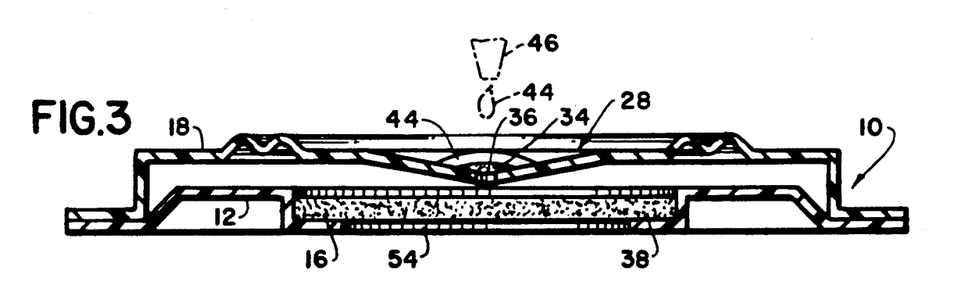
FIGS. 3, 4 and 5 are cross-sectional views similar to FIG. 2, and showing stages in performing a test using the analytical device of FIG. 2.
Figure 4:
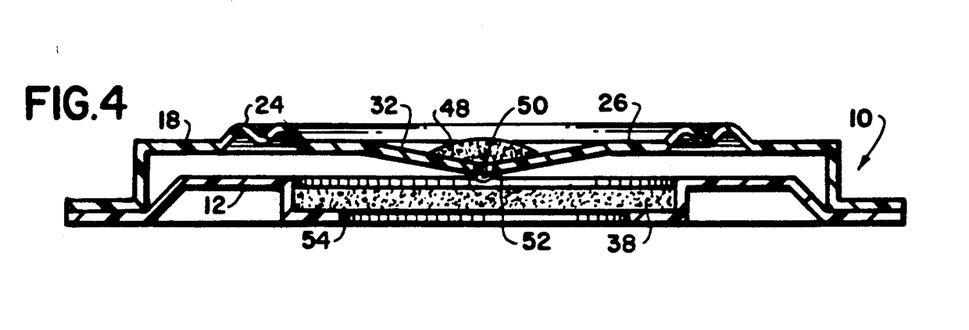
Figure 5:
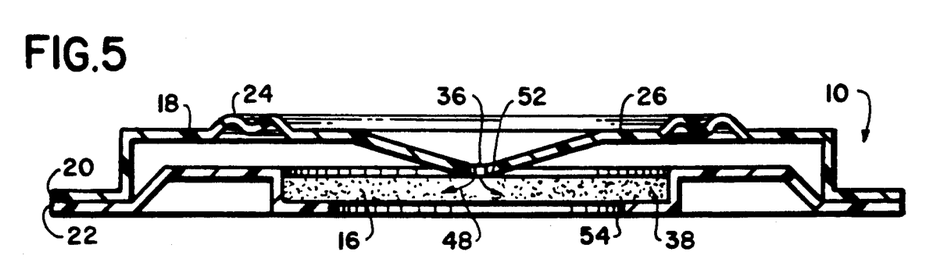

The sequence of operation in performing an assay utilizing the analytical device 10 is illustrated in FIGS. 3-5. An aliquot 44 of test sample (shown in phantom) is deposited in the reaction well 28 as shown in FIG. 3. The device of the present invention is suitable for analysis of relatively small volume test samples, e.g. 10 to 50 microliters. The drop of test sample may be discharged from a pipette tip 46 into which sample has been aspirated in a previous step as part of an analysis sequence performed by an automated clinical analyzer. It will be appreciated that such automated analysis systems are generally known in the art and the automated clinical analyzer does not form a part of the present invention. In general, such automated analyzers are adapted to measure a characteristic of a sample fluid deposited on the analysis device and may include a device supply means, metering means for depositing a predetermined gravity of sample on the device, incubator means, device transfer means for moving the analysis device from the incubator means, and a read station wherein the characteristic can be measured. Typical of such analyzers are those disclosed in U.S. Pat. Nos. 4,295,069, 4,296,070, 4,512,952 and 4,568,517, all assigned to the Eastman Kodak Company. Alternatively, the aliquot 44 of test sample may be manually pipetted from a larger volume of test sample onto the device. The liquid test sample 44 will react with the dried reaction component 34 to reconstitute the same to form a combined liquid test sample and reaction mixture identified generally as 48 in FIG. 4.

The reaction mixture 48 will flow, under the influence of gravity and capillary action into the opening 36 to form a meniscus 50. The surface tension of the liquid reaction mixture 48 and the walls of the reaction well 28 and walls of the opening 36 will prevent the reaction mixture 48 from flowing through the opening 36 onto the porous member 16.

After a suitable time interval sufficient to allow the desired specific interaction between the test sample 44 and the reaction component 34 to run substantially to completion, manual or mechanical pressure is then applied to cover 18, preferably within circumferential corrugation 24 to move the reaction well 28 to the transfer position shown in FIG. 5, such movement permissible due to the inherent flexibility of the cover 18 as may be enhanced by the corrugations 24. In this transfer position, the circumferential lip 52 of the opening 36 engages porous member 16 and the liquid meniscus 50 comes into fluid engagement with porous member 16. The reaction mixture 48 will flow through opening 36 by capillary action due to the hydrophilic, open structure of the porous member. The liquid reaction mixture 48 will be absorbed and dispersed within porous member 16, whereupon the analyte in the test sample will interact with the analyte responsive substance dispersed therein with the resultant generation of a detectable response indicative of the presence and concentration of analyte in the test sample.

The base 12 is provided with an appropriate viewing port 54 through which the detectable response in the porous member 16 can be observed.

Figure 7:
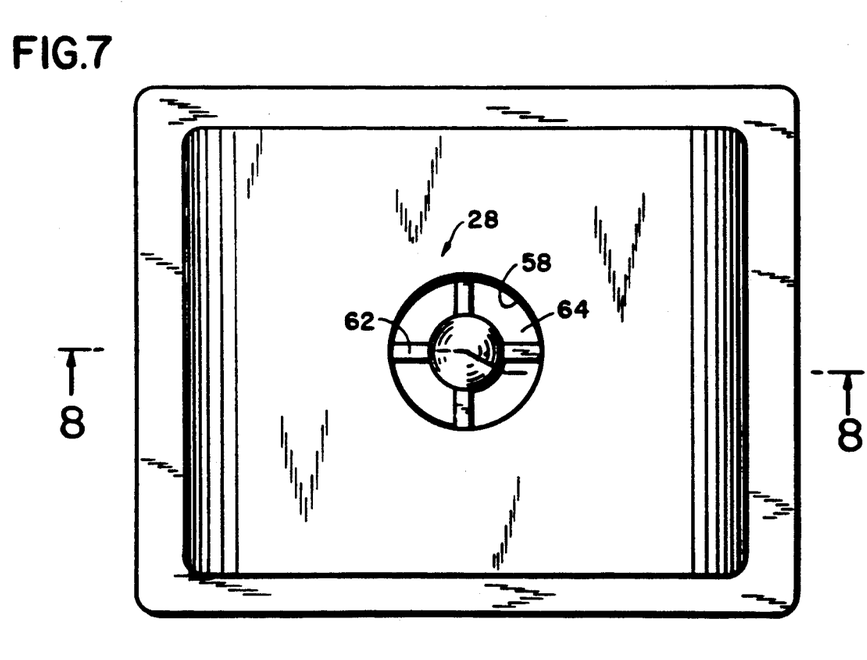
FIG. 7 is a top plan view of an analytical device constructed in accordance with an alternative embodiment of our invention.
Figure 8:
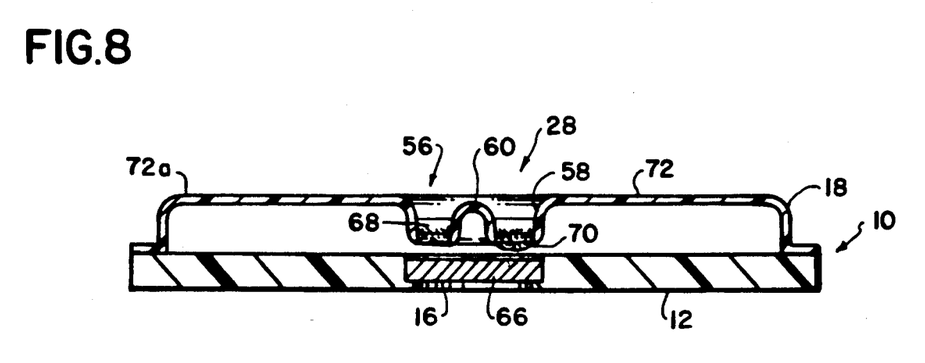
FIGS. 8 and 9 are cross-sectional views taken generally along line 8—8 in FIG. 7 and showing stages in performing a test using the analytical device of FIG. 7.
Figure 9:
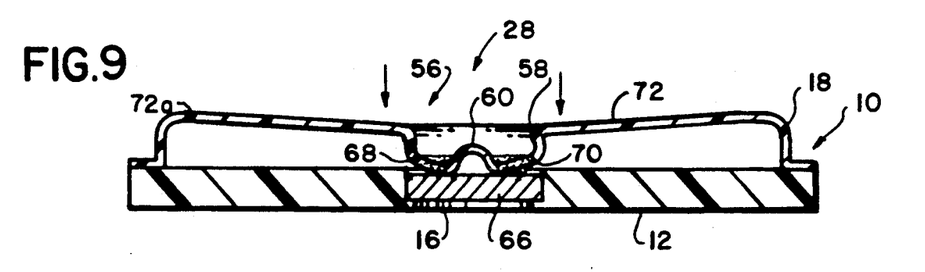

A modified form of the analytical device shown in FIGS. 7, 8 and 9 is similar in many respects to that shown in FIGS. 1-5 and like reference numerals designate like parts. In the form of FIGS. 7-9, the reaction well is an annular depression 56 in the cover 18 created by generally upright circular wall 58. A central dome-like projection 60 is connected to the wall 58 by a plurality of circumferentially spaced webs 62 having openings 64 therebetween. Preferably, the top of the dome-like projection 60 lies below the top surface of the cover 18 so that the devices may be stacked one on top of the other in a magazine or cassette without the bottom of one device contacting the projection on the device upon which it rests. The openings 64 function in a like manner to opening 36, being sized such that surface tension between the liquid received or retained in the reagent well normally prevents the liquid from passing therethrough.

The analytical device 10 of FIGS. 7, 8 and 9 is prepared and used in the same manner as explained with reference to the device illustrated in FIGS. 1-5. At least one dry analyte responsive substance 66 is contained within the porous member 16. A reaction component 68 is contained within the reaction well 28. To perform an assay, an aliquot of the test solution 44 is deposited within the reaction well 28, preferably, directly over the dome-like projection 60 so that the same acts to disperse the test sample uniformly throughout the reaction well to reconstitute and mix with the reagent component 68 contained therein. The liquid reagent mixture retained in the reaction well forms meniscus 70. Mechanical or manual pressure may be exerted on the central area 72 immediately surrounding the reagent well for moving webs 62 and openings 64 into engagement with porous member 16 as shown in FIG. 9. As in the embodiment discussed hereinabove, the thickness of the material forming the cover 18 may provide the necessary flexibility permitting such downward travel. Flexibility may also be provided at the shoulders 72a. The liquid meniscus 70 within each opening 62 thereby engages porous member 16, resulting in the liquid reaction mixture within the reaction well flowing into porous member 16 by capillary action. Alternatively, pressure may be exerted directly on the dome-like projection 60, however, this is not believed desirable in the case of automated clinical analyzers due to the possibility of reaction mixture carryover caused by the pressure applying mechanism coming into contact with successive reaction mixtures of successive analytical devices as downward force is applied to the projections.

It will be appreciated that the downward travel of projection 60 is facilitated by the inherent flexibility of the material forming the cover 18 and the webs 62.

Figure 10:
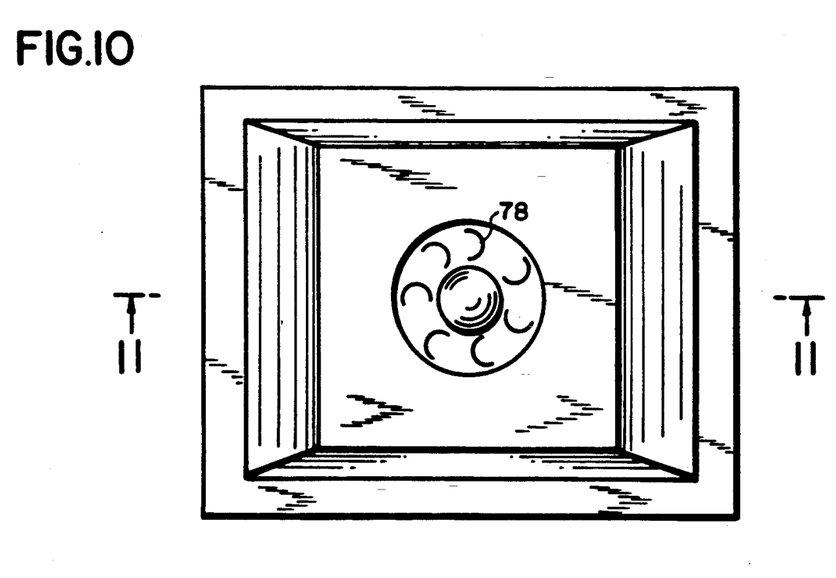
FIG. 10 is a top plan view of an analytical device constructed in accordance with yet another embodiment of our invention.
Figure 11:
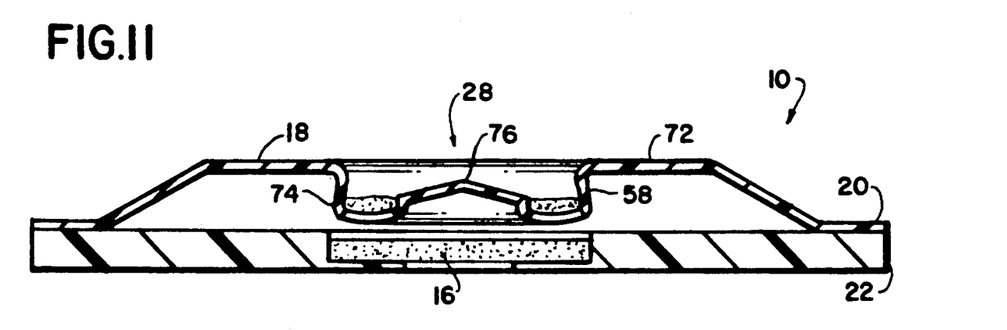
FIGS. 11 and 12 are cross-sectional views taken generally along line 11—11 in FIG. 10 showing stages in performing a test using the analytical device of FIG. 10.
Figure 12:
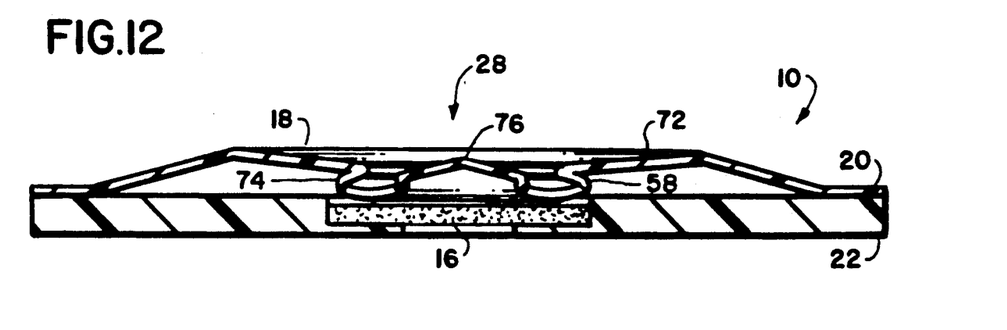

The analytical device of the present invention can be used in automated clinical analyzers. It has been found that during the sequence of operation, the individual analytical elements are subject to vibrational and other forces which may overcome the forces retaining the liquid in the reaction well of the previously described embodiments. Accordingly, in another embodiment of our present invention means are provided to effectively reduce the effects such system forces may have in dislodging the reaction mixture from the reaction well. This further modification of our invention is shown in FIGS. 10, 11 and 12 will be readily understood to be similar in many respects to the embodiment shown in FIGS. 7-9. Like reference numerals designate like parts.

Figure 13:
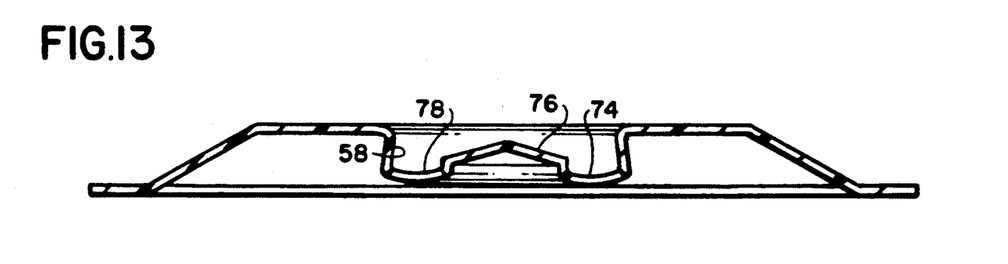
FIG. 13 is an enlarged sectional view through a portion of the device of FIG. 10.

In this alternative embodiment, the reaction well is provided with a transverse wall which effectively serves as a bottom and the side walls are configured to reduce unwanted reaction mixture spillage due to system vibration, translational or other forces acting on the device. With reference to FIGS. 11 and 13, the wall 58 of the reaction well 28 has a slightly downwardly divergent configuration, i.e., the diameter of the reaction well 28 increases with the depth of the reaction well (as is shown greatly exaggerated in FIG. 13). A transverse wall 74, which may be of generally concave cross-sectional configuration as shown, is connected to the circular wall 58. Centrally disposed in the reaction well is a frusto-conical projection 76. The top of the frusto-conical projection 76, as with the dome-like projection 60, lies beneath the top surface of the cover 18. Likewise, when a drop of test sample is deposited on the frusto-conical projection 76, the latter acts to disperse the test sample uniformly throughout the reaction well.

The transverse wall 74 is provided with one or more arcuate slits 78 which are normally effectively closed. Preferably, in order to provide suitable flexibility, the slits may extend into the reaction well wall as shown in FIG. 13. When the central area 72 of the cover member 18 is depressed (FIG. 12), the transverse wall 74 due in part to its concave cross-sectional configuration, is sufficiently deformed so that the slits 78 open, permitting the reaction mixture to flow by the influence of gravity, through the slits 78 and to contact the porous member 18 and be drawn therethrough by capillary attraction.

Figure 14A:
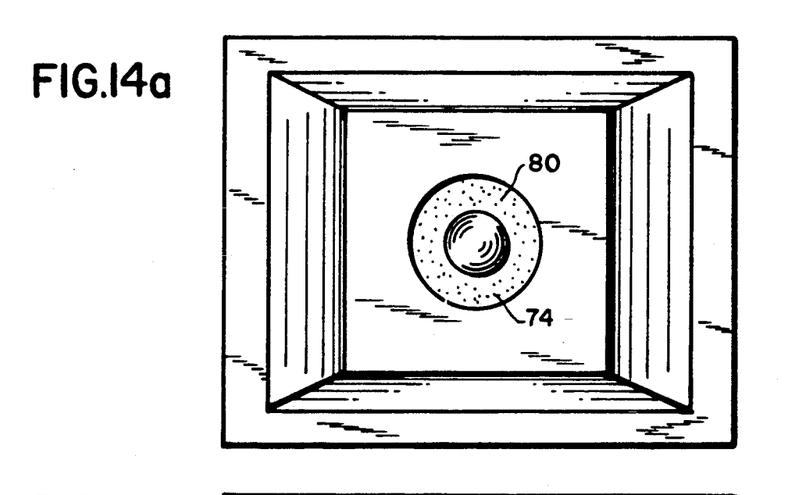
FIGS. 14A and 14B are top plan views of analytical devices constructed in accordance with still other embodiments of our invention.
Figure 14B:
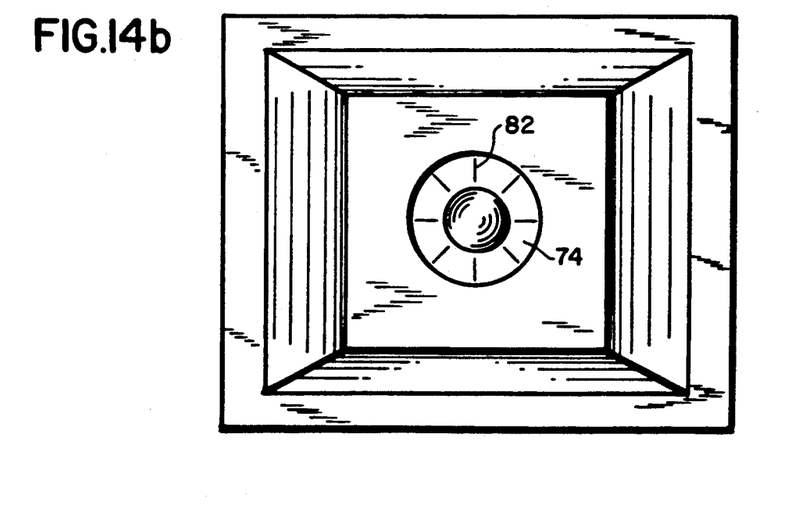
Figure 15:
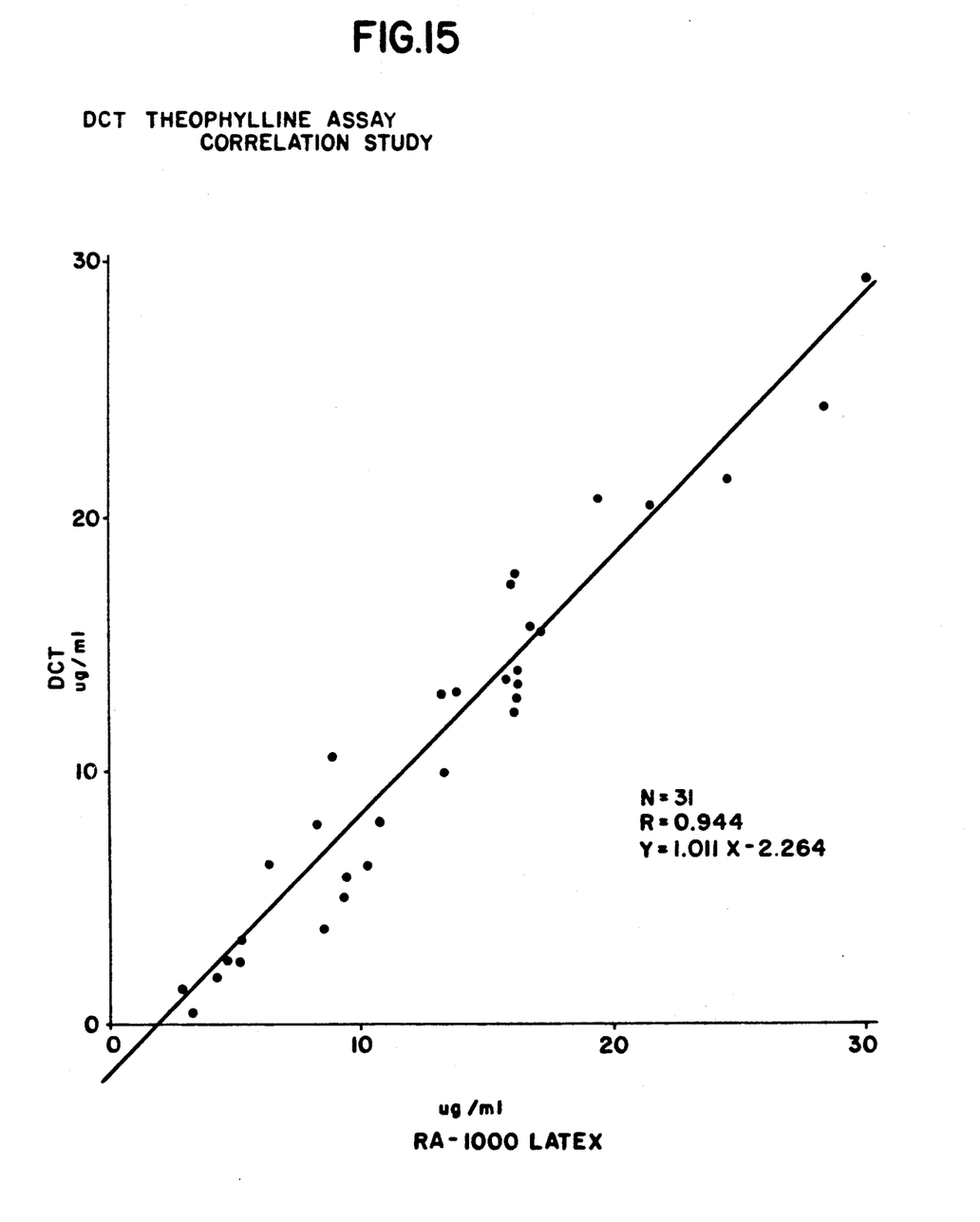
FIG. 15 is a scatter plot of the correlation between assay results for the concentration of theophylline in a solution recorded in a test utilizing an analytical device constructed in accordance with the present invention as compared with an assay pursuant to the Technicon Latex Turbidimitry method.

FIGS. 14a and 14b show various modifications which may substitute for the arcuate slits 78 shown in FIG. 10. Alternatively, a multiplicity of holes 80 (FIG. 14a) or radial slits 82 (FIG. 14b) may be provided in the transverse wall 74.

As noted hereinabove, the analytical device of our invention is adapted for containing two substances or reagents initially in spaced relationship from one another, and thereafter bringing these substances into fluid contact in the presence of a liquid test sample to perform an assay.

The analytical device of our present invention is constructed to permit a wide variety of assays to be performed by varying the reaction components and analyte responsive substances contained thereon. For example, the sample may have to be pretreated by exposure to a reaction component for a certain time period before exposing it to further reagents. In such instances, the reaction component can include a substance which physically changes the sample, such as a cytolytic agent, to release an analyte for detection. For example, where the analyte is hemoglobin the substance can be a cytolytic agent, such as a surfactant. The surfactant can, for example, include polyoxyethylene ethers of aliphatic alcohols such as Brij surfactants (ICI United States, Wilmington, Del.), polyoxyethylene derivatives of sorbitol anhydrigde fatty acid partial esters such as Tween surfactants (ICI United States, supra) and alkylaryl polyethers of alcohols, sulfonates, or sulfates such as Triton surfactants (Rohm & Haas Company, Philadelphia, Pa.).

A surfactant may be placed in the reaction well 28 and a hemoglobin reactive substance in the porous member 16. Similarly, the chylomicrons in serum samples can be broken up first by the action of a surfactant in the reaction well before triglyceride is reacted with triglyceride responsive substances in the porous member 16.

Clinical diagnostic tests frequently involve several reactive components such as the reaction component and the analyte responsive component. The reaction component may be responsive to the analyte to form a reaction product and the analyte responsive substance effects a detectable response to the reaction product. The reaction component may contain expensive enzymes or labile biological substances which are susceptible to denaturing or degradation by the analyte responsive substance due to incompatible pH, ionic strength or chemistry if kept together. Therefore, the reaction component can be made more stable by means of physical segregation from the analyte responsive substance. The analytical device of the subject invention can provide such segregation or compartmentalization of reactive components. The reaction component may be stored as $R_1$ in the reaction well 28 and the analyte responsive substance as $R_2$ in the porous member 16.

Where the analyte is glucose, the test sample may first be reacted with glucose oxidase in the reaction well on the cover. The hydrogen peroxide produced can then react with peroxidase together with a redox indicator to produce a detectable colorimetric response in the porous member.

Similarly, where the analyte is cholesterol, the test sample may first be reacted with cholesterol esterase and cholesterol oxidase in the reaction well before the peroxidase reaction is initiated in the porous member.

When an interfering species is present in the test sample, it may be removed first by an agent in the reaction well. For such application, the agent can be a chemical substance that reacts specifically with the interfering species only. For example, as demonstrated in Example 2 hereinbelow, in the case of ascorbic acid interference in clinical serum samples, ascorbate oxidase may be placed in the reaction well to destroy the ascorbic acid before the analyte is reacted to give a detectable response in the porous member. In the case of protein interference in total bilirubin analysis, diphylline or caffeine can be placed in the reaction well to displace bilirubin from protein binding in serum sample first before it is reacted with diazosulfanilic acid in the porous member.

Alternatively the reaction component and analyte responsive substance may comprise reagents for a homogeneous specific binding assay system which produces a detectable response that is a function of the presence of the analyte in the sample. Such homogeneous specific binding assay systems can include a label which participates in an enzymatic reaction. More particularly, one preferred format of the homogeneous specific binding assay reagent and system include an antibody which binds the analyte, a conjugate of the analyte or a binding analog thereof and a label, and a detection system which interacts with the label to produce a detectable response that is different when the label conjugate is bound by the antibody compared to when it is not so bound. Any of the various label systems which are known to be suitable for use in homogeneous immunoassays are applicable for use in the present device and method.

In still another application of the subject invention is the use of substances in the reaction well to filter out or absorb undesirable material in the test sample. For example, the reaction well can be packed with activated charcoal or absorbent known in the art of chromatography to selectively remove interfering substances in the test sample-e. Or it can be packed with fiberglass or other filtering aids which can hold back blood cells from whole blood samples or cell debris and salt crystals from urine samples. In this case, the passage or opening 36 in the well must be sized to retain the filtering material, but allow the interference free test sample to pass through when the reaction well is push to contact with the porous element.

As previously noted, the reagent systems which can be used provide, or can be readily adapted to provide, a detectable response, such as a color change, related to the presence or amount of the analyte under assay in the liquid sample. The porous element of the invention provides enhanced electro-magnetic radiation signals such as a change in light reflectance in the visible spectrum, thereby producing a visible color change, or a change in light reflectance outside the visible range such as in the ultraviolet range or infrared range. The detectable response is one which can be observed through the senses directly or by use of ancillary detection means, such as a spectrophotometer or other sensing means. After the analytical result is obtained as a detectable change, it is measured, usually by passing the analytical device through a field in which suitable apparatus for reflectance measurement is provided. Such apparatus serves to direct a beam of energy, such as light, which is then reflected from the element back to a detector. Generally, electro-magnetic radiation in the range of from about 200 to about 900 nm has been found useful for such measurements.

By measuring the detectable response produced by the analyte responsive substance and comparing the detectable response so produced with the detectable response produced when the analysis is conducted with a series of standard compositions containing known amounts of analyte, the qualitative and quantitative determination of analyte in the test sample can be made.

The following working examples describe experiments which were performed in developing the present invention. Standard commercially available reagent grade chemicals were used whenever possible. These examples are to be considered illustrative of the present invention and should not be interpreted as limiting its scope.

EXAMPLE 1

The object of this experiment is to illustrate the utility of the analytical device of FIGS. 1–5 of the subject invention in determining the presence of theophylline in serum.

The analytical devices comprised components thermoformed from PVC sheet material. The base 12 had a thickness of 0.020 inch; the cover 18 a thickness of 0.010 inch, and the porous member, obtained from Porex Technologies of Fairburn, Ga., had a thickness of one thirty second (1/32) of an inch and an average 35 micron pore size.

Two reagents, $R_1$ and $R_2$, were formulated. $R_1$ corresponded to the reaction component 34; $R_2$ corresponded to the analyte responsive substance 38.

$R_1$ contained the following: 0.05M imidazole - HCl buffer pH 7.5, 0.6 mM magnesium acetate, 0.2 mM EDTA, 0.5 mg/ml IgG, 0.49 IU/ml diaphorase, 4 IU/ml glucose-6-phosphate dehydrogenase, 2.4 IU/ml phosphoglucomutase, 104 IU/L phosphoacetyl glucomutase, 10 ul/ml purified monoclonal antibody to theophylline (Beckman Lot #706022), 1% Dextran $T_{70}$ and 5% mannitol. The Commission of Enzymes of the International Union of Biochemistry has defined an International Unit (IU) of enzyme activity as 1 micromole (umol) of substrate utilized per minute under specified conditions of pH and temperature.

$R_2$ contained the following: 1 mM glucose-1-phosphate, 2 mM NAD, 0.5 mM p-iodonitrotetrazolium violet, 0.23 uM theophylline glucosamine diphosphate conjungate and 4% hydroxypropyl methyl cellulose.

Analytical devices were prepared by depositing thirty-five microliters of each of $R_1$ and $R_2$ into the reagent well 24 and porous member 16 respectively of each device. The reagent impregnated devices were lyophilized, and then sealed in individual foil pouches and kept under refrigeration.

Pooled serum samples were used to prepare theophylline standards. Thirty-five microliters of the serum standard diluted 1:100 were pipetted onto the reaction well 28, and the lyophilized $R_1$ was allowed to dissolve completely to form a reaction mixture in a period of three minutes. By means of a plunger, the reagent well was then manually brought into contact with the porous member 18 for five seconds, during which time all the reaction mixture was transferred to the porous member 16 by capillary action.

The diffused reflectance optical density at 500 nm was monitored off the underside of the porous member 16 over a period of five minutes. The change in optical density between the one and three minute interval was plotted against the concentration of theophylline.

Thirty-one clinical serum samples containing various levels of theophylline were used as unknowns and their values were computed from the standard curve. The results were compared to those obtained pursuant to a commercial latex turbidity method run on the TECHNICON RA-1000 clinical analysis system (TECHNICON RA-1000 is a registered trademark of Technicon Instruments Corporation, Tarrytown, N.Y.). The correlation coefficient was 0.944, the slope was 1.011 and the intercept was −2.264 (see FIG. 13).

The results obtained utilizing the analytical device thus compared favorably with those of a commercial latex method.

EXAMPLE 2

The following example demonstrates the use of the device of FIGS. 10-13 of our invention to eliminate ascorbic acid interference from uric acid analysis in a sequential reaction scheme. It is known that ascorbic acid can occur in serum in high concentrations which can cause significant error in clinical tests.

The analytical devices comprised components thermoformed from high impact polystyrene sheet material. The base 12 had a thickness of 0.060 inches; the cover 18 a thickness of 0.010 inches, and the porous member 16, obtained from Porex Technologies of Fairburn, Ga., a thickness of one thirty second (1/32) of an inch and a average 50 micron pore size.

Two reagents, $R_1$ and $R_2$ were formulated. $R_1$ was placed in the reaction well 28 and $R_2$ on the hydrophilic porous member 16.

$R_1$ contained an agent which was able to destroy the interferent when the test sample was placed in contact with it. In this example, ascorbate oxidase was used to react with ascorbic acid in the test sample to remove the interferent.

$R_1$ contained the following: 100,000 IU/L ascorbate oxidase, 2.5 gm/L bovine serum albumin, and 50 gm/L mannitol.

$R_2$ contained the following: 375,000 IU/L horse radish proxidase, 40,000 IU/L uricase, 25 gm/L bovine serum albumin, 50 gm/L 4-amino antipyrene, 75 gm/L sodium, p-hydroxybenzoate, 10 gmL hydroxypropyl methyl cellulose, 20 mM sodium azide, 1 mM EDTA, and 0.2M phosphate buffer, pH 8.5.

Twenty microliters of each reagent were deposited onto the devices. The reagent impregnated devices were lyphilized and kept in a desiccator.

Aqueous standards containing 0, 5, 10, 15 and 20 mg/dl uric acid were prepared and used to establish a standard curve. An analytical sample containing 10 mg/dl uric acid plus 10 gm/dl ascorbic acid was also prepared. Tests were performed to compare the efficiency of (i) the analytical device 10 in which ascorbate oxidase was contained in $R_1$ and reacted first with the sample, with the sample $R_1$ reaction mixture then exposed to $R_2$ (Device 1 hereinbelow) to (ii) a device in which the cover 18 was removed, and the ascorbate oxidase reacted concurrently with $R_2$ on the sample (Device 2). Measurements were performed using twenty microliters of standard or sample. For Device 1, the analytical sample was introduced to the reaction well 28 and allowed to incubate with the ascorbate oxidase. Then the reaction well 28 was brought into contact with the porous member 16 by means of a plunger. A five second contact time was sufficient to transfer all the fluid from the reaction well to the hydrophilic porous member 16. For Device 2, the test solutions were placed directly in the hydrophilic porous member impregnated with $R_2$. The diffused reflectance optical density at 540 nm was monitored off the underside of the porous member over a period of five minutes at 37° C. on an InfraAnalyzer 300 reflectance spectrometer (Technicon Instruments Corporation, Tarrytown, N.Y.), which was modified to cover the spectral range between 340 and 700 nm. The optical density at the end of five minutes was recorded.

The recovered values of uric acid in the test sample containing 10 mg/dl ascorbic acid interferent were computed from the standard curve.

The result is summarized in Table 1. A 100% recovery of the uric acid value was obtained with ascorbate oxidase in $R_1$ on the analytical device whereas use of ascorbate oxidase in $R_2$ alone recovered only 67% of the uric acid value. This clearly demonstrates that the device of this invention is very effective in removing interferents in analytical samples or providing a sequential reaction mechanism.

TABLE 1

| Recovered uric acid values in sample containing 10 mg/dl ascorbic acid | | | |
|---|---|---|---|
| Theoretical Value | No Ascorbate Oxidase | Device 2 Ascorbate Oxidase in $R_2$ | Device 1 Ascorbate Oxidase in $R_1$ |
| 10.0 mg/dl | 0.3 mg/dl | 6.7 mg/dl | 10.0 mg/dl |

Some advantages of the present invention evident from the foregoing description include an analytical test device which maintains two substances or reagents initially in spaced relationship from one another, and thereafter is adopted to bring these substances into fluid contact either sequentially or concurrently with each other in the presence of a liquid test sample to perform an assay. Both substances may be present in a dry form, and reconstituted by the liquid test sample.

In view of the above, it will be seen that the several objects of our invention are achieved and other advantageous results attained.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. An analytical device for the quantitative and qualitative determination of an analyte in a liquid test sample, said analytical device comprising:
   a) a base means;
   b) a porous member received in said base means;
   c) at least one analyte responsive substance which undergoes a detectable response to the presence and concentration of analyte dispersed throughout said porous member;
   d) a reaction component;
   e) a cover means integral with said base means permanently affixed in a superimposed spaced relationship thereto;
   f) a reaction well in said cover means for storing said reaction component and adapted to receive liquid test sample whereby said liquid test sample and said reaction component form a liquid reaction mixture within said reaction well;
   g) passage means in said reaction well for transferring said reaction mixture therethrough, said passage means normally being in a spaced superimposed relationship to said porous member and effectively closed to transfer therethrough of said reaction mixture, and said passage means being selectively movable toward said porous member to effectively open to passage therethrough of said reaction mixture to said porous member whereby said analyte responsive substance will undergo a detectable response to said analyte present in said liquid reaction mixture; and
   h) said base means provided with an observation port exposing said porous member for observing any detectable response of said analyte responsive substance;
   i) wherein said cover means includes a central portion, said reaction well positioned within said central portion and deflective means in the form of a deformable circumferential corrugation around said central portion integral with said center portion and said cover means to impart flexibility of said central portion in said cover means so that said central portion may be displaced towards said porous member.

2. The apparatus of claim 1 wherein said passage means is normally open and is sized such that surface tension of said liquid reaction mixture with said reaction well prevents said liquid reaction mixture held in said reaction well from transfer through said passage means.

3. The apparatus of claim 2 wherein said liquid reaction mixture held by said reaction well is drawn through said passage means by capillary attraction when said passage means is moved into engagement with said porous member.

4. The apparatus of claim 1 wherein said reaction well is a conical depression in said cover means.

5. The apparatus of claim 1 wherein said reaction component is a dry substance within said reaction well and is reconstituted upon contact with said liquid test sample.

6. An analytical device for the quantitative and qualitative determination of an analyte in a liquid test sample, said analytical device comprising:
   a) a base means;
   b) a porous member received in said base means;
   c) at least one analyte responsive substance which undergoes a detectable response to the presence and concentration of analyte dispersed throughout said porous member;
   d) a reaction component;
   e) a cover means integral with said base means permanently affixed in a superimposed spaced relationship thereto;
   f) a reaction well in said cover means for storing said reaction component and adapted to receive liquid test sample whereby said liquid test sample and said reaction component form a liquid reaction mixture within said reaction well;
   g) passage means in said reaction well for transferring said reaction mixture therethrough, said passage means normally being in a spaced superimposed relationship to aid porous member and effectively closed to transfer therethrough of said reaction mixture, and said passage means being selectively movable toward said porous member to effectively open to passage therethrough of said reaction mixture to said porous member whereby said analyte responsive substance will undergo a detectable response to said analyte present in said liquid reaction mixture; and
   h) said base means provided with an observation port exposing said porous member for observing any detectable response of said analyte responsive substance;
   i) wherein said reaction well is a cylindrical depression in said cover means and said passage means includes a projection centrally positioned within said cylindrical depression and at least two support arms extending from said projection to said reaction well defining openings therebetween.

7. The apparatus of claim 6 wherein said reaction component is a dry substance within said reaction well and is reconstituted upon contact with said liquid test sample.

8. An analytical device for the quantitative and qualitative determination of an analyte in a liquid test sample, said analytical device comprising:
   a) a base means;
   b) a porous member received in said base means;
   c) at least one analyte responsive substance which undergoes a detectable response to the presence and concentration of analyte dispersed throughout said porous member;
   d) a reaction component;
   e) a cover means integral with said base means permanently affixed in a superimposed spaced relationship thereto;
   f) a reaction well in said cover means for storing said reaction component and adapted to receive liquid test sample whereby said liquid test sample and said reaction component form a liquid reaction mixture within said reaction well;
   g) passage mans in said reaction well for transferring said reaction mixture therethrough, said passage means normally being in a spaced superimposed relationship to said porous member and effectively closed to transfer therethrough of said reaction mixture, and said passage means being selectively movable toward said porous member to effectively open to passage therethrough of said reaction mixture to said porous member whereby said analyte responsive substance will undergo a detectable response to said analyte present in said liquid reaction mixture; and
   h) said base means provided with an observation port exposing said porous member for observing any detectable response of said analyte responsive substance;

i) wherein said reaction well is a cylindrical depression in said cover means and said passage means includes a projection centrally positioned within said cylindrical depression and a transverse wall extending from said projection to said reaction well and having openings therein normally substantially closed to fluid passage therethrough.

9. The apparatus of claim 8 wherein said reaction component is a dry substance within said reaction well and is reconstituted upon contact with said liquid test sample.

* * * * *